United States Patent
Ding et al.

(10) Patent No.: US 11,921,049 B2
(45) Date of Patent: *Mar. 5, 2024

(54) PYROPHOSPHOROLYSIS ACTIVATED FLUORESCENCE TO MEASURE PAP AMPLIFICATION OF NUCLEIC ACID

(71) Applicants: Shaofeng Ding, Santa Fe Springs, CA (US); Qiang Liu, Rancho Cucamonga, CA (US)

(72) Inventors: Shaofeng Ding, Santa Fe Springs, CA (US); Qiang Liu, Rancho Cucamonga, CA (US)

( * ) Notice: Subject to any disclaimer, the term of this patent is extended or adjusted under 35 U.S.C. 154(b) by 392 days.

This patent is subject to a terminal disclaimer.

(21) Appl. No.: 16/658,029

(22) Filed: Oct. 19, 2019

(65) Prior Publication Data
US 2020/0150047 A1    May 14, 2020

Related U.S. Application Data

(60) Provisional application No. 62/757,767, filed on Nov. 9, 2018.

(51) Int. Cl.
| | | |
|---|---|---|
| *C12Q 1/68* | (2018.01) | |
| *C12Q 1/6844* | (2018.01) | |
| *G01N 21/76* | (2006.01) | |

(52) U.S. Cl.
CPC .......... *G01N 21/76* (2013.01); *C12Q 1/6844* (2013.01)

(58) Field of Classification Search
None
See application file for complete search history.

(56) References Cited

U.S. PATENT DOCUMENTS

| | | | | |
|---|---|---|---|---|
| 2004/0009515 A1* | 1/2004 | Liu | ...................... | C12Q 1/6858 435/6.12 |
| 2007/0219361 A1* | 9/2007 | Bodepudi | ............ | C12Q 1/6827 536/23.1 |
| 2010/0112565 A1* | 5/2010 | Tobler | .................. | C12Q 1/6858 435/6.1 |
| 2010/0227320 A1* | 9/2010 | Fu | ........................ | C12Q 1/6858 435/6.12 |
| 2013/0310269 A1* | 11/2013 | So | .......................... | C12Q 1/686 506/9 |
| 2014/0186840 A1* | 7/2014 | Ding | ........................ | C12Q 1/68 435/6.12 |
| 2014/0274774 A1* | 9/2014 | Li | ........................ | C12Q 1/6858 506/9 |
| 2015/0126373 A1* | 5/2015 | Yen | ...................... | C12Q 1/6883 506/9 |
| 2015/0307917 A1* | 10/2015 | Walder | ..................... | C12N 9/22 435/6.12 |
| 2017/0191051 A1* | 7/2017 | Nikiforov | ...... | C12Y 207/07007 |

* cited by examiner

*Primary Examiner* — Suryaprabha Chunduru (57) ABSTRACT

A new fluorescence detection method called pyrophosphorolysis activated fluorescence was developed to measure PAP amplification of nucleic acid. A fluorophore-quencher dual-attached blocked primer was used for PAP which has a fluorophore attached to a nucleotide in the internal region or at the 5' end and a quencher attached to a blocked nucleotide at the 3' end. Multiple fluorophore-quencher dual-labeled blocked primers were also used for multiplex PAP, which are attached with different fluorophores to distinguish multiple templates in a reaction.

8 Claims, 2 Drawing Sheets

Specification includes a Sequence Listing.

SEQUENCE LISTING

<160> NUMBER OF SEQ ID NOS: 7

<210> SEQ ID NO 1
<211> LENGTH: 27
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is HEX-dAMP
<220> FEATURE:
<221> NAME/KEY: misc_feature
<222> LOCATION: (27)..(27)
<223> OTHER INFORMATION: n is TAMRA-ddCMP

<400> SEQUENCE: 1
nctctgagcc ctctttccaa actactn                                27

<210> SEQ ID NO 2
<211> LENGTH: 27
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is ddCMP

<400> SEQUENCE: 2
actctgagcc ctctttccaa actactn                                      27

<210> SEQ ID NO 3
<211> LENGTH: 28
<212> TYPE: DNA
<213> ORGANISM: Aids-associated retrovirus
<220> FEATURE:
<221> NAME/KEY: misc_feature
<222> LOCATION: (11)..(11)
<223> OTHER INFORMATION: n is FAM-dTMP
<220> FEATURE:
<221> NAME/KEY: misc_feature
<222> LOCATION: (28)..(28)
<223> OTHER INFORMATION: n is TAMRA-ddUMP

<400> SEQUENCE: 3
ttggaggaca ncaagcagcc atgcaaan                                     28

<210> SEQ ID NO 4
<211> LENGTH: 28
<212> TYPE: DNA
<213> ORGANISM: Aids-associated retrovirus
<220> FEATURE:
<221> NAME/KEY: misc_feature
<222> LOCATION: (1)..(1)
<223> OTHER INFORMATION: n is FAM-dTMP
<220> FEATURE:
<221> NAME/KEY: misc_feature
<222> LOCATION: (28)..(28)
<223> OTHER INFORMATION: n is TAMRA-ddUMP

<400> SEQUENCE: 4
ntggaggaca tcaagcagcc atgcaaan                                     28

<210> SEQ ID NO 5
<211> LENGTH: 27
<212> TYPE: DNA
<213> ORGANISM: Aids-associated retrovirus
<220> FEATURE:
<221> NAME/KEY: misc_feature
<222> LOCATION: (27)..(27)
<223> OTHER INFORMATION: n is ddTMP

<400> SEQUENCE: 5
tgctatgtca gttcccttg gttctcn                                       27

<210> SEQ ID NO 6
<211> LENGTH: 28
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is ddCMP

<400> SEQUENCE: 6
gtctcaaaga ttccagaagt cagtacan                                     28

<210> SEQ ID NO 7
<211> LENGTH: 28
<212> TYPE: DNA
<213> ORGANISM: Homo sapiens
<220> FEATURE:

```
<221> NAME/KEY: misc_feature
<222> LOCATION: (28)..(28)
<223> OTHER INFORMATION: n is ddCMP

<400> SEQUENCE: 7
gtctcaaaga ttccagaagt caggaaan                                            28
```

PYROPHOSPHOROLYSIS ACTIVATED FLUORESCENCE TO MEASURE PAP AMPLIFICATION OF NUCLEIC ACID

CROSS-REFERENCE TO RELATED APPLICATIONS

This non-provisional application claims priority from U.S. provisional patent application No. 62/757,767, filed on Nov. 9, 2018.

SEQUENCE LISTING

This application is being filed along with a Sequence Listing and its electronic format entitled SequenceListing.txt.

BACKGROUND OF THE INVENTION

Field of the Invention

The present invention relates to the field of molecular biology and particularly pyrophosphorolysis activated polymerization (PAP) for nucleic acid amplification.

Description of the Prior Art

Pyrophosphorolysis Activated Polymerization (PAP)

Pyrophosphorolysis activated polymerization (PAP) is a method for nucleic acid amplification where pyrophosphorolysis and polymerization are serially coupled by DNA polymerase using 3' blocked primers (Liu and Sommer, 2000; Liu and Sommer, 2004b). A primer is blocked at the 3' end with a non-extendable nucleotide (3' blocker), such as a dideoxynucleotide, and cannot be directly extended by DNA polymerase. When the 3' blocked primer anneals to its complementary DNA template, DNA polymerase can remove the 3' blocker from the 3' blocked primer in the presence of pyrophosphate or its analog, which reaction is called pyrophosphorolysis. The DNA polymerase can then extend the 3' unblocked primer on the DNA template. In addition to references cited herein, PAP has been described in U.S. Pat. Nos. 6,534,269, 7,033,763, 7,105,298, 7,238,480, 7,504,221, 7,914,995, and 7,919,253.

The serial coupling of pyrophosphorolysis and extension using the 3' blocked primer in PAP results in an extremely high selectivity (Liu and Sommer, 2004a; Liu and Sommer, 2004b) because a significant nonspecific amplification (Type II error) requires mismatch pyrophosphorolysis followed by mis-incorporation by the DNA polymerase, an event with a frequency estimated to be $3.3 \times 10^{-11}$.

The bi-directional form of PAP (Bi-PAP) is especially suitable for allele-specific amplification that uses two opposing 3' blocked primers with a single nucleotide overlap at their 3' ends (Liu and Sommer, 2004a; Liu and Sommer, 2004b). Bi-PAP can detect one copy of a mutant allele in the presence of $10^9$ copies of the wild type DNA without false positive amplifications.

DNA-PAP

PAP was initially tested with Tfl and Taq polymerases using DNA template of the human dopamine D1 gene, proving the principle that DNA-dependent DNA pyrophosphorolysis and DNA-dependent DNA polymerization can be serially coupled (Liu and Sommer, 2000). The efficiency of PAP was greatly improved using TaqFS, a genetically engineered polymerase comprising a F667Y mutation, which were demonstrated using other DNA templates (Liu and Sommer, 2002).

RNA-PAP

RNA-PAP was developed that can directly amplify RNA template without additional treatment. RNA-PAP brings in a new mechanism for amplification of RNA template in which RNA-dependent DNA pyrophosphorolysis removes 3' blocker such as 3' dideoxynucleotide from a blocked primer when hybridized to RNA template, and then RNA-dependent DNA polymerization extends the activated primer. Due to this serial coupling, RNA-PAP has high selectivity against mismatches on the RNA template, providing highly specific amplification of RNA template (U.S. Pat. No. 9,133,491).

PAP with Acycolonucleotide Blocker and Type II Polymerase

We showed that Type II DNA polymerase efficiently catalyzes template-dependent pyrophosphorolysis to activate primers blocked at their 3' termini with acyclonucleotides in which a 2-hydroxyethoxymethyl group substitutes for the 2'-deoxyribofuranosyl sugar. Type II DNA polymerases Vent (exo-) and Pfu (exo-) were used for PAP with acyclonucleotide-blocked primers, besides Type I DNA polymerase (Liu and Sommer, 2004c).

Multiplex-PAP

Advantageous to produce little or no primer-dimer or false priming (Liu and Sommer, 2002), multiple pairs of primers ($\geq 2$) were used to amplify multiple potential templates ($\geq 2$) located at multiple loci ($\geq 2$) in one reaction (Liu, et al., 2006). In an example, multiplex PAP used eight pairs of primers that targeted eight loci in human genome including seven different exons scattered along a 30 Kb sequence of the human factor IX gene and one exon in the human ATM gene.

Multiplex PAP can also uses multiple pairs of blocked primers to amplify multiple almost-sequence-identical templates located in one locus in a single reaction, among which the sequence differences may be as little as one base substitution, a few base deletion or insertion, such as in the KRAS gene (US patent application publication 20180265919).

Current Fluorescence Methods to Measure Amplification of Nucleic Acid

Currently, fluorescent chemistries available can be categorized into two major types: 1) DNA-binding dyes (such as SYBR Green I), and 2) dye-labeled, sequence-specific oligonucleotide primers or probes (such as TaqMan probe).

SYBR Green I exhibits little fluorescence when free in solution, but its emitted fluorescence increases up to 1,000-fold strength when binds nonspecifically to double-stranded DNA.

The advantages include simple assay design (probe is not necessary), lower cost, and melt-curve analysis to check specific amplified product. However, a major drawback is nonspecific binding to double-stranded DNA, such as dimmers, and non-multiplexing.

TaqMan probe is typically an oligonucleotide with a fluorophore covalently attached to a nucleotide at the 5' end, and a quencher to a nucleotide at the 3' end. The quencher molecule quenches the fluorescence emitted by the fluorophore through a mechanism of Förster resonance energy transfer (FRET) (Holland et al., 1991).

In PCR amplification, when Taq polymerase extends a primer, its 5'-3' exonuclease activity hydrolyzes the probe that has annealed to template. Thus, the hydrolysis releases the fluorophore from the quencher to emit fluorescence.

The main advantages include high specificity, high signal-to-noise ratio, and multiplexing because multiple probes can have different fluorophores to differentiate multiple templates in a single reaction.

A New Fluorescence Detection Method and its Advantages

A method of pyrophosphorolysis activated fluorescence was developed to measure PAP amplification of nucleic acid. A single fluorophore-quencher dual-labeled blocked primer was used for singleplex PAP, which has a fluorophore attached to a nucleotide in the internal region or at the 5' end and a quencher attached to a blocked nucleotide at the 3' end. Multiple fluorophore-quencher dual-labeled blocked primers were used for multiplex PAP, which are attached with different fluorophores to distinguish multiple templates in a reaction.

SUMMARY OF THE INVENTION

Form I of Fluorophore-Quencher Dual-Labeled Blocked Primer

For a pair of forward and reverse blocked primers (Form I) for pyrophosphorolysis activated polymerization to amplify a template, the forward or reverse blocked primer has a fluorophore attached to a nucleotide in the internal region or at the 5' end and a quencher attached to a blocked nucleotide at the 3' end.

Once the blocked nucleotide attached with the quencher is removed by pyrophosphorolysis, the fluorophore generates a detectable fluorescence signal in PAP amplification.

The forward or reverse blocked primer has a FAM (carboxyfluorescein) or HEX (hexachlorofluorescein) fluorophore attached to a nucleotide in the internal region or at the 5' end and a TAMRA (carboxytetramethylrhodamine) quencher attached to a dideoxynucleotide at the 3' end.

Once the dideoxynucleotide attached with the TAMRA (carboxytetramethylrhodamine) quencher is removed by pyrophosphorolysis, the FAM (carboxyfluorescein) or HEX (hexachlorofluorescein) fluorophore generates a detectable fluorescence signal in PAP amplification.

Of the forward or reverse blocked primer, emission spectrum of the fluorophore overlaps absorbance spectrum of the universal quencher.

Of the forward or reverse blocked primer, the fluorophore is 30 bases or less from the 3' end.

The forward or reverse blocked primer has an artificial mutation introduced into the 3' region, which can delay the product accumulation to a later time or cycle in a method called delayed-PAP.

The artificial mutation is a single base substitution.

The artificial mutation ranges from the $3^{rd}$ base to the 5th base from the 3' end.

A plurality of pairs of forward and reverse blocked primers (Form I) for pyrophosphorolysis activated polymerization to amplify a plurality of templates in a reaction comprise:

a) for a first pair of forward and reverse primers to amplify a first template, the forward or reverse blocked primer has a first fluorophore attached to a nucleotide in the internal region or at the 5' end and a universal quencher attached to a first blocked nucleotide at the 3' end, and b) for a second pair of forward and reverse primers to amplify a second template, the forward or reverse blocked primer has a second fluorophore attached to a nucleotide in the internal region or at the 5' end and the same universal quencher attached to a second blocked nucleotide at the 3' end.

Once the first blocked nucleotide attached with the universal quencher is removed by pyrophosphorolysis, the first fluorophore generates a detectable fluorescence signal in PAP amplification, and once the second blocked nucleotide attached with the same universal quencher is removed by pyrophosphorolysis, the second fluorophore generates another detectable fluorescence signal in PAP amplification.

For the plurality of pairs of forward and reverse blocked primers, the forward or reverse primers of the first and second pairs have the same universal quencher but the different first and second fluorophores.

For the plurality of pairs of forward and reverse blocked primers, the forward or reverse blocked primer of the first pair has a FAM (carboxyfluorescein) fluorophore attached to a nucleotide in the internal region or at the 5' end and a universal TAMRA quencher attached to a first dideoxynucleotide at the 3' end, and the forward or reverse blocked primer of the second pair has a HEX (hexachlorofluorescein) fluorophore attached to a nucleotide in the internal region or at the 5' end and the same universal TAMRA (carboxytetramethylrhodamine) quencher attached to a second dideoxynucleotide at the 3' end.

Once the 3' dideoxynucleotides attached with the universal TAMRA (carboxytetramethylrhodamine) quencher are removed by pyrophosphorolysis, the FAM (carboxyfluorescein) and HEX (hexachlorofluorescein) fluorophores generate detectable fluorescence signals in PAP amplification.

For the plurality of pairs of forward and reverse blocked primers, the first template is an internal control and the second template is a target.

For the plurality of pairs of forward and reverse blocked primers, emission spectrums of the fluorophores overlaps absorbance spectrum of the universal quencher.

For the plurality of pairs of forward and reverse blocked primers, the fluorophores are 30 bases or less from the 3' ends.

For the plurality of pairs of forward and reverse blocked primers, the forward or reverse blocked primer of a pair of forward and reverse primers has an artificial mutation introduced into the 3' region, which can delay the product accumulation to a later time or cycle in a method called delayed-PAP.

Of the forward or reverse blocked primers, the artificial mutation is a single base substitution.

Of the forward or reverse blocked primer, the artificial mutation ranges from the $3^{rd}$ base to the 5th base from the 3' end.

A method for multiplex pyrophosphorolysis activated polymerization in which a plurality of pairs of forward and reverse blocked primers (Form I) to amplify a plurality of templates in a reaction comprises:

a) for a first pair of forward and reverse primers to amplify a first template, the forward or reverse blocked primer has a first fluorophore attached to a nucleotide in the internal region or at the 5' end and a universal quencher attached to a first blocked nucleotide at the 3' end, b) once the first blocked nucleotide attached with the universal quencher is removed by pyrophosphorolysis, the first fluorophore generates a detectable fluorescence signal in PAP amplification,
c) for a second pair of forward and reverse primers to amplify a second template, the forward or reverse blocked primer has a second fluorophore attached to a nucleotide in the internal region or at the 5' end and the same universal quencher attached to a second blocked nucleotide at the 3' end, and
d) once the second blocked nucleotide attached with the universal quencher is removed by pyrophosphorolysis, the second fluorophore generates a detectable fluorescence signal in PAP amplification.

Form II of Fluorophore-Quencher Dual-Labeled Blocked Primer

For a pair of forward and reverse blocked primers (Form II) for pyrophosphorolysis activated polymerization to amplify a template, the forward or reverse blocked primer has a fluorophore attached to a blocked nucleotide at the 3' end and a quencher attached to a nucleotide in the internal region or at the 5' end.

Once the blocked nucleotide attached with the fluorophore is removed by pyrophosphorolysis, the fluorophore generates a detectable fluorescence signal in PAP amplification.

A plurality of pairs of forward and reverse blocked primers (Form II) for pyrophosphorolysis activated polymerization to amplify a plurality of templates in a reaction comprise:
a) for a first pair of forward and reverse primers to amplify a first template, the forward or reverse blocked primer has a first fluorophore attached to a first blocked nucleotide at the 3' end and a universal quencher attached to a nucleotide in the internal region or at the 5' end,
b) for a second pair of forward and reverse primers to amplify a second template, the forward or reverse blocked primer has a second fluorophore attached to a second blocked nucleotide at the 3' end and the same universal quencher attached to a nucleotide in the internal region or at the 5' end, and Once the first blocked nucleotide attached with the first fluorophore is removed by pyrophosphorolysis, the first fluorophore generates a detectable fluorescence signal in PAP amplification, and once the second blocked nucleotide attached with the second fluorophore is removed by pyrophosphorolysis, the second fluorophore generates another detectable fluorescence signal in PAP amplification.

A method for multiplex pyrophosphorolysis activated polymerization in which a plurality of pairs of forward and reverse blocked primers (Form II) to amplify a plurality of templates in a reaction comprises:
a) for a first pair of forward and reverse primers to amplify a first template, the forward or reverse blocked primer has a first fluorophore attached to a first blocked nucleotide at the 3' end and a universal quencher attached to a nucleotide in the internal region or at the 5' end,
b) once the first blocked nucleotide attached with the first fluorophore is removed by pyrophosphorolysis, the first fluorophore generates a detectable fluorescence signal in PAP amplification,
c) for a second pair of forward and reverse primers to amplify a second template, the forward or reverse blocked primer has a second fluorophore attached to a second blocked nucleotide at the 3' end and the same universal quencher attached to a nucleotide in the internal region or at the 5' end, and
d) once the second blocked nucleotide attached with the second fluorophore is removed by pyrophosphorolysis, the second fluorophore generates a detectable fluorescence signal in PAP amplification.

BRIEF DESCRIPTION OF THE DRAWINGS

Panel A shows format I of fluorophore-quencher dual-labeled blocked primer. A fluorophore (F), such as FAM, is covalently attached to a nucleotide in the internal region or at the 5' end, and a quencher (Q), such as TAMRA, is covalently attached to a blocked nucleotide at the 3 end, such as dideoxynucleotide. In PAP amplification, once the primer anneals to its complementary template, pyrophosphorolysis removes the 3' non-extendable, blocked nucleotide covalently attached with the quencher, releasing the fluorophore from quencher to emit fluorescence (indicated by a star symbol), and then polymerization extends the unblocked primer.

Panel B shows format II of fluorophore-quencher dual-labeled blocked primer. A fluorophore (F) is covalently attached to a blocked nucleotide at the 3' end and a quencher (Q) is covalently attached to a nucleotide at the 5' end or in the internal region.

FIG. 2. Pyrophosphorolysis Activated Fluorescence in Simpleplex and Multiplex PAP Assays Panel A illustrates simpleplex PAP in the GNAS gene. The GNAS PAP assay includes a forward fluorophore-quencher dual-labeled blocked primer (SEQ ID 1) and a reverse blocked primer (SEQ ID 2) (Table 2) in a reaction. In PAP amplification, a HEX fluorescence signal was generated and measured. The amplification plot is showed with the cycle number in X-axis and relative fluorescence unit in y-axis for the given cycle.

Panel B illustrates simpleplex PAP in the HIV gene. The HIV PAP assay includes a forward fluorophore-quencher dual-labeled blocked primer (SEQ ID 3) and a reverse blocked primer (SEQ ID 5) (Table 2) in a reaction. In PAP amplification, a FAM fluorescence signal was generated and measured.

Panel C illustrates multiplex PAP in the GNAS and HIV genes. The multiplex PAP assay contains the forward fluorophore-quencher dual-labeled blocked primer and reverse blocked primer (SEQ ID 1 and 2) for the GNAS gene, and the fluorophore-quencher dual-labeled blocked primer and reverse blocked primer (SEQ ID 3 and 5) for the HIV gene in a reaction. In PAP amplification, HEX and FAM fluorescence signals were generated and measured.

DETAILED DESCRIPTION OF THE INVENTION

Terminology of PAP Technology

Unless defined otherwise, all technical and scientific terms used herein have the same meaning as commonly understood by one of ordinary skill in the art.

PCR refers to polymerase chain reaction.

Pyrophosphorolysis is the reverse reaction of deoxyribonucleic acid polymerization. In the presence of pyrophosphate, the 3' nucleotide is removed by a polymerase from duplex DNA to generate a triphosphate nucleotide and a 3' unblocked duplex DNA: $[dNMP]_n+PPi \rightarrow [dNMP]_{n-1}+dBTP$ (Deutscher and Kornberg, 1969).

Polymerase or nucleic acid polymerase refers to a polymerase characterized as polymerization or extension of deoxyribonucleic acids.

3' blocked primer refers to an oligonucleotide with a 3' non-extendable nucleotide (3' blocker), such as a dideoxynucleotide or an acycolonucleotide. The 3' nucleotide could not be directly extended, but it can be removed by pyrophosphorolysis and then the unblocked primer can be extended by polymerase.

PAP refers to pyrophosphorolysis activated polymerization.

Delayed pyrophosphorolysis activated polymerization (delayed-PAP) means that the product starts to accumulate at later time or cycle in the amplification process.

Bidirectional-PAP (Bi-PAP) is a form of PAP that uses a pair of opposing blocked primers that overlap by one nucleotide at their 30 termini.

Exponential-PAP is a form of PAP that uses a pair of two opposing forward and reverse primers for exponential product accumulation with cycles. At least one primer is blocked primer.

Sensitivity or detection limit is defined as the smallest copy number of a template that generates a detectable product when the blocked primers match the template at the targeted nucleotide, such as the 3' end.

Specificity is defined as the largest copy number of a template that generates an undetectable product when the blocked primers mismatch the template at the targeted nucleotide, such as the 3' end.

Selectivity, the ratio of sensitivity to specificity, is defined as the ability to detect a small number of copies of the matched template in the presence of a large number of copies of the mismatched template without causing false positives.

Thermostable enzyme refers to an enzyme that is heat stable or heat resistant.

TaqFS is a genetic engineered form of Taq polymerase containing G46E and F667Y amino acid changes compared with the wild type sequence. In PAP, it has 5'-3' polymerase activity that can incorporate dNTP in extension, and pyrophosphorolysis activity that can remove ddNMP from the 3' end of a primer, but no 5'-3' exonuclease activity.

PAP polymerase is a genetic engineered form of Taq polymerase containing F667Y amino acid changes compared with the wild type sequence. It has 5'-3' polymerase activity and pyrophosphorolysis activity.

A pair of primers means two opposing forward and reverse primers.

Singleplex PAP means that one pair of primers amplify one template in a reaction.

Multiplex PAP means that ≥2 pairs of primers amplify ≥2 potential templates in a reaction. The multiple templates may be located at multiple loci or at one locus. The sequence differences among the templates, may be as little as one base substitution, a few base deletion or insertion, and may be located as near as at the same nucleotide. In addition, the templates may be completely or partially overlapped within the region.

The 5' region of a primer is the 5' part of the primer sequence, such as the ten successive nucleotides from the 5' end.

The 3' region of a primer is the 3' part of the primer sequence, such as the ten successive nucleotides from the 3' end.

The internal region is the primer sequence between the 5' end and the 3' end.

The central region of a primer is the middle part of the primer sequence between the 5' region and the 3' region.

Starting template means the template which is present before amplification starts, such as those of plasmid and genomic DNA.

Terminology of Fluorophore and Quencher

Fluorophore: a molecule, such as FAM, HEX, and TET, that displays fluorescence. The fluorescence is generated when the fluorophore absorbs light energy at a short wavelength and then emits light energy at a longer wavelength. Each fluorophore has a characteristic absorbance spectrum and a characteristic emission spectrum. The specific wavelength at which a fluorophore will most efficiently absorb energy is called the peak absorbance and the wavelength at which it will most efficiently emit energy is called the peak emission.

FAM is a fluorophore which has peak absorbance at 492 nm wavelength and peak emission at 520 nm wavelength.

HEX is a fluorophore which has peak absorbance at 535 nm wavelength and peak emission at 556 nm wavelength.

TET is a fluorophore which has peak absorbance at 521 nm wavelength and peak emission at 536 nm wavelength.

Quencher: a molecule, such as TAMRA, that decreases fluorescence intensity of a fluorophore report. It has a characteristic absorbance spectrum with a peak absorbance. For a quencher to function through a mechanism of a mechanism of fluorescence-resonance energy transfer (FRET), its absorbance spectrum overlaps the emission spectrum of the fluorophore, and its distance is proximate enough to the fluorophore, such as no more than 30 bases on a oligonucleotide.

TAMRA is a quencher which has peak absorbance 575 nm.

Universal quencher: a molecule, such as TAMRA, that decreases fluorescence intensities of two or more types of fluorophores.

Single fluorophore-labeled primer: a fluorophore, such as FAM, HEX, and TET, is covalently attached to a nucleotide at the 5' end, or in the internal region, or at the 3' end.

Single quencher-labeled primer: a quencher, such as TAMRA, is covalently attached to a nucleotide at the 5' end, or in the internal region, or at the 3' end.

Fluorophore-quencher dual-labeled primer: there are two formats: 1) a fluorophore, such as FAM, HEX, and TET, is covalently attached to a nucleotide at the 5' end or in the internal region, and a quencher, such as TAMRA, is covalently attached to a nucleotide at the 3' end, and 2) a fluorophore, such as FAM, HEX, and TET, is covalently attached to a nucleotide at the 3' end, and a quencher, such as TAMRA, is covalently attached to a nucleotide at the 5' or in the internal region.

Terminology of Real-Time Fluorescence Detection

Baseline is the level of fluorescence signal during initial cycles. The low level can be considered as background or "noise" of the reaction.

Threshold is defined as the level of fluorescence signal that is a significant higher than baseline signal and can distinguish amplification signal from the background.

Ct (threshold cycle) is the cycle number at which the fluorescence signal crosses the threshold.

Terminology of Delayed-PAP

3'-perfect-match primer means the 3' region has no artificial mutations and perfectly matches the starting template.

Artificial mutation means the mutation that is artificially introduced into primer sequences.

Artificial mismatch is formed between the artificial mutation in the 3' region of a 3'-artificial-mutation primer and the complementary strand of a template.

3'-artificial-mutation primer means an artificial mutation is introduced into the 3' region.

Regular-PAP means PAP with two 3'-perfect-match primers. PAP means regular-PAP unless stated otherwise.

Simplex regular-PAP means PAP with two 3'-perfect-match primers. Simplex PAP means simplex regular-PAP unless stated otherwise.

Multiplex regular-PAP means all PAP assays are regular-PAP assays in the multiplex format. Multiplex PAP means multiplex regular-PAP unless stated otherwise.

Delayed-PAP means PAP with one or two 3'-artificial-mutation primers to delay the product accumulation to a later time or cycle.

Multiplex delayed-PAP means at least one delayed-PAP assay in the multiplex format.

Figure 1:
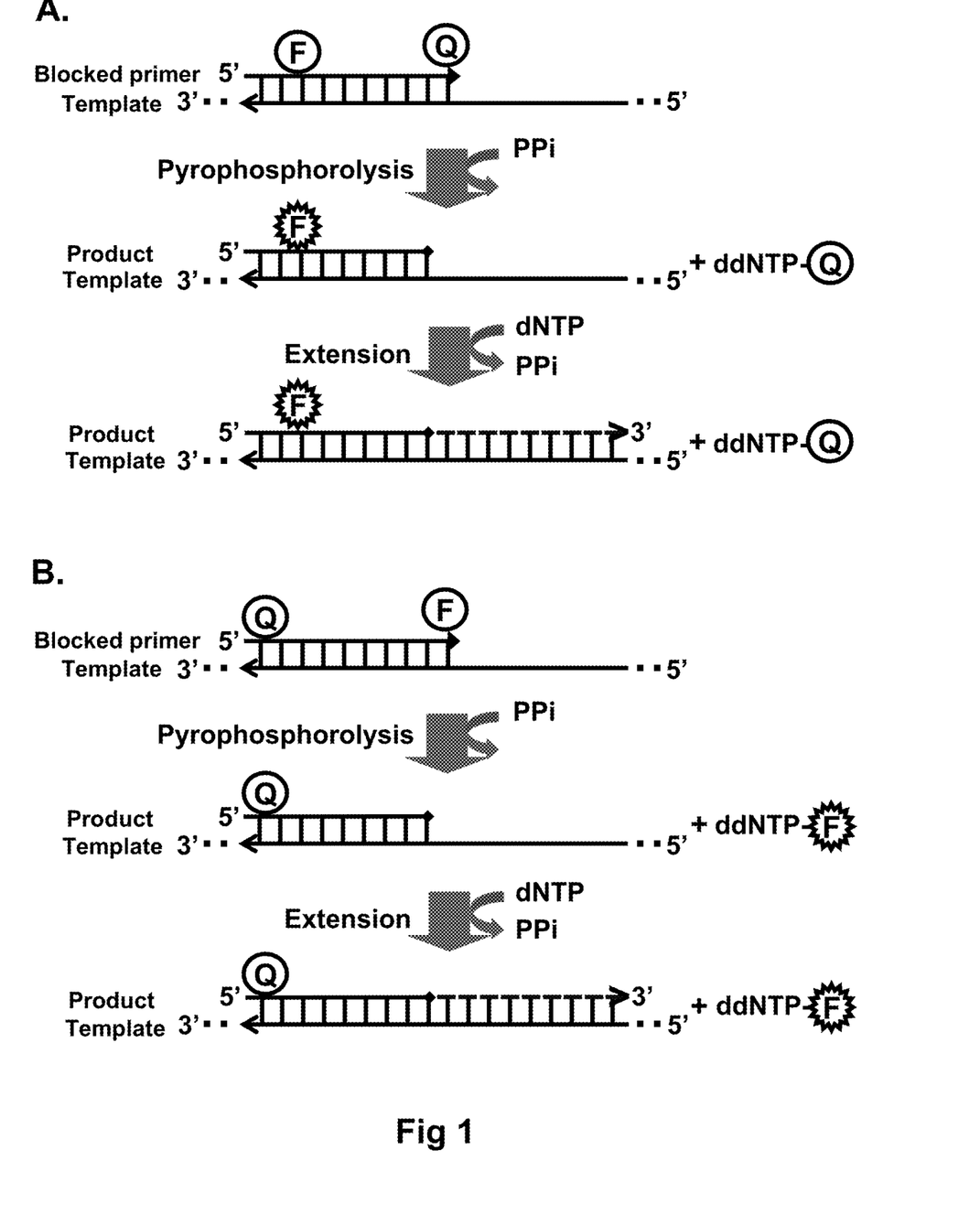
FIG. 1. Principle of Pyrophosphorolysis Activated Fluorescence

Principle of Pyrophosphorolysis Activated Fluorescence to Measure PAP Amplification of Nucleic Acid 1) Fluorophore-Quencher Dual-Labeled Blocked Primer For format I of fluorophore-quencher dual-labeled blocked primer, a fluorophore, such as FAM, HEX, and TET, is covalently attached to a nucleotide at the 5' end or in the internal region, and a quencher, such as TAMRA, is covalently attached to a blocked nucleotide at the 3' end, such as dideoxynucleotide (FIG. 1A).

The FAM, HEX, TET, and TAMRA have peak absorbances at 492 nm, 535 nm, 521 nm, 552 nm wavelengths, respectively; and peak emissions at 520 nm, 556 nm, 536 nm, 575 nm wavelengths, respectively. The absorbance spectrum of the TAMRA quencher overlaps the emission spectrums of the FAM, HEX, and TET fluorophores. Thus, multiplex fluorophore-quencher dual-labeled blocked primers may have different fluorophores but the same universal quencher.

Other types of fluorophores, quenchers such as Dark Quenchers, and 3' blocked nucleotides such as acyclonucleotide are also applicable, once they are satisfied by 1) the absorbance spectrum of the quencher overlaps the emission spectrum of the fluorophore, 2) the distance from the quencher to the fluorophore is ≤30 nucleotides so that the quencher can substantially quench the fluorophore, and 3) the 3' blocked nucleotide covalently attached with the quencher can be removed by pyrophosphoresis in PAP.

For format II of fluorophore-quencher dual-labeled blocked primer, a fluorophore, such as FAM, HEX, and TET, is covalently attached to a blocked nucleotide at the 3' end, such as dideoxynucleotide, and a quencher, such as TAMRA, is covalently attached to a nucleotide at the 5' or in the internal region (FIG. 1B).

2) Pyrophosphorolysis Activated Fluorescence

Within structure of a fluorophore-quencher dual-labeled blocked primer, through a mechanism of fluorescence-resonance energy transfer (FRET) from the fluorophore to the quencher, the fluorophore is kept from emitting fluorescence.

In PAP amplification, once the fluorophore-quencher dual-labeled blocked primer (Format I) anneals to its complementary template, pyrophosphorolysis removes the 3' non-extendable, blocked nucleotide which is covalently attached with the quencher such as TATRA, releasing and thus activating the fluorophore such as FAM from the quencher to emit fluorescence, and then polymerization extends the 3' unblocked primer (FIG. 1A).

In addition, different fluorophore-quencher dual-labeled blocked primers can have different fluorophores such as FAM, HEX, and TET but one universal quencher such as TAMRA to differentiate multiple templates in a single reaction.

The number of released fluorophore is equal to the number of fluorophore-quencher dual-labeled blocked primer exhausted, and also to the number of amplified product, a 1:1:1 relationship. Furthermore, each of them is directly proportional to intensity of the emitted fluorescence. These are true to both single and multiple fluorophore-quencher dual-labeled blocked primers.

As for format II of fluorophore-quencher dual-labeled blocked primer, the mechanism also includes pyrophosphorolysis to release and thus activate the fluorophore to emit fluorescence (FIG. 1B).

Besides other advantages, pyrophosphorolysis activated fluorescence should be specific to the amplified product because it needs pyrophosphorolysis, an enzyme catalyzed chemical reaction involving covalent bond change, to release and thus activate the fluorophore. It should also be efficient because the number of the released fluorophore accumulates exponentially in PAP amplification.

Furthermore, the differences between pyrophosphorolysis activated fluorescence (Format I) and Taqman probe (Holland et al., 1991) are compared in Table 1.

TABLE 1

Comparison between pyrophosphorolysis activated fluorescence and Taqman probe

|  | Pyrophosphorolysis activated fluorescence | Taqman probe |
| --- | --- | --- |
| Associated technology | PAP amplification | PCR amplification |
| Assay composition for one amplicon | Two blocked primers only | Two regular primers and one probe |
| Structure to generate fluorescence | A fluorophore-quencher dual-labeled blocked primer | A fluorophore-quencher dual-labeled probe |
| Mechanism to generate fluorescence | Pyrophosphorolysis of quencher at the 3' blocked nucleotide of the primer | Hydrolysis of fluorophore at the 5' nucleotide of the probe |
| Multiplexing | Yes | Yes |
| Polymerase activities required | Pyrophosphorolysis and 5'-3' polymerization activities | 5'-3' polymerization and 5'-3' exonuclease activities |

TABLE 1-continued

Comparison between pyrophosphorolysis activated fluorescence and Taqman probe

| | Pyrophosphorolysis activated fluorescence | Taqman probe |
|---|---|---|
| Fluorescence accumulation mode | Exponential with cycles, the number of released fluorophore = the number of amplified product | Super-exponential with cycles, the number of released fluorophore ≠ the number of amplified product |

Example 1 of Materials and Methods

Preparation of Primers

3' ddCMP blocked primers were chemically synthesized in 3'-5' direction and purified by HPLC by Integrated DNA Technologies.

3' ddAMP, ddTMP and ddGMP blocked primers were synthesized enzymatically by adding ddATP, ddTTP and ddGTP to the 3' ends of oligodeoxynucleotides by terminal transferase (Liu and Sommer, 2000; Liu and Sommer, 2002).

5' end or internal single dye (FAM, HEX) labeled primers were chemically synthesized in 3'-5' direction and purified by HPLC by Integrated DNA Technologies.

Rhodamine dye labeled dideoxynucleotide analogs or terminators of TAMRA-ddATP, TAMRA-ddUTP, TAMRA-ddGTP, and TAMRA-ddCTP were purchased from PerkinElmer Life Sciences, in which TAMRA is attached to the base of the nucleotide through a covalent bond. Then they were added to the 3' ends of the single dye labeled primers by terminal transferase to synthesize dual dye labeled blocked primers.

Finally they were purified by 7M urea/16% polyacrylamide gel electrophoresis. The amount of each recovered primer was determined by UV absorbance at 260 nm.

Preparation of Templates

Genomic DNA was extracted from blood white cells using QIAamp Blood Mini Kit according to Qiagen's protocol.

Recombinant plasmid DNA was constructed by inserting into pUC57 vector a 300 bp HIV-1 target DNA segment which was chemically synthesized. After transformed into *E. coli*, the recombinant plasmid DNA was extracted using QIAamp Plasmid Mini Kit according to Qiagen's protocol.

The eluted DNA was dissolved in TE buffer (10 mM Tris-HCl, 0.1 mM EDTA, pH 8.0) and its amount was determined by UV absorbance at 260 nm.

PAP Reaction

Unless stated otherwise, each reaction mixture of 20 µl contained 88 mM Tris-HCl (pH 8.0 at 25° C.), 10 mM $(NH_4)_2SO_4$, 2 mM $MgCl_2$, 25 µM each dNTP (dATP, dTTP, dGTP and dCTP), 0.1 µM each of primers, 150 µM $Na_4PP_i$, starting DNA template of the wildtype genomic DNA and/or plasmid DNA, and 1 units of polymerase for PAP amplification.

Thermocycling and Fluorescence Detection

A Bio-Rad CFX96 real-time PCR detection system was used for amplification. A cycling entailed 96° C. for 12 seconds, 60° C. for 30 seconds, 64° C. for 30 seconds, and 68° C. for 30 seconds for a total of 45 cycles. A denaturing step of 96° C. for 2 min was added before the first cycle.

Analysis mode: fluorophore, Baseline setting: baseline subtracted curve fit, Threshold cycle (Ct) determination: single threshold, Baseline method: Auto calculated, Threshold setting: auto calculated. Filter mode was selected for FAM and/or HEX fluorescence detections. Ct value was thus measured for each reaction which is proportional to the amount of amplified product in the early exponential phase of amplification.

Example 2 of Singleplex and Multiplex-Pap Assays of the Gnas and Hiv Genes

Singleplex and multiplex PAP assays of the GNAS and HIV genes were used to demonstrate how pyrophosphorolysis activated fluorescence works.

GNAS and HIV genes are chosen as target and control because HIV-1 viral DNA can integrate into human genome and thus their detection from genomic DNA isolated from blood white cells is a medical need.

A singleplex PAP assay was tested with a forward fluorophore-quencher dual-labeled blocked primer (SEQ ID 1) and a reverse blocked primer (SEQ ID 2) in the GNAS gene (Table 2). The fluorophore-quencher dual-labeled blocked primer (SEQ ID 1) contains a HEX fluorophore covalently attached to a dAMP at the 5' end, and a TAMRA quencher covalently attached to a ddCMP at the 3' end. When the GNAS gene was amplified form 100,000 copies of the human wildtype genomic DNA (i.e., 330 ng), a HEX fluorescence signal was generated and measured at Ct 20.5 (FIG. 2A), the cycle number at which the HEX fluorescence signal crossed the threshold of 87 fluorescence units. In addition for the non-template control, no HEX fluorescence signal was seen above the threshold, showing the specificity.

Another singleplex PAP assay was tested with a forward fluorophore-quencher dual-labeled blocked primer (SEQ ID 3) and a reverse blocked primer (SEQ ID 5) in the HIV gene (Table 2). The fluorophore-quencher dual-labeled blocked primer contains a FAM fluorophore covalently attached to a dTMP at the 11th nucleotide from the 5' end (SEQ ID 3) and a TAMRA quencher covalently attached to a ddUMP at the 3' end. When the HIV gene was amplified form 100 copies of the HIV plasmid DNA template, a FAM fluorescence signal was generated and measured at Ct 32.2 (FIG. 2B), the cycle number at which the FAM fluorescence signal crossed the threshold of 122 fluorescence units. Another forward fluorophore-quencher dual-labeled blocked primer (SEQ ID 4) was also tested with a similar result, which contains a FAM fluorophore covalently attached to a dTMP at the 5' end and a TAMRA quencher covalently attached to a ddUMP at the 3' end. In addition, no FAM fluorescence signal was seen above the threshold in the non-template control, showing the specificity.

Figure 2:
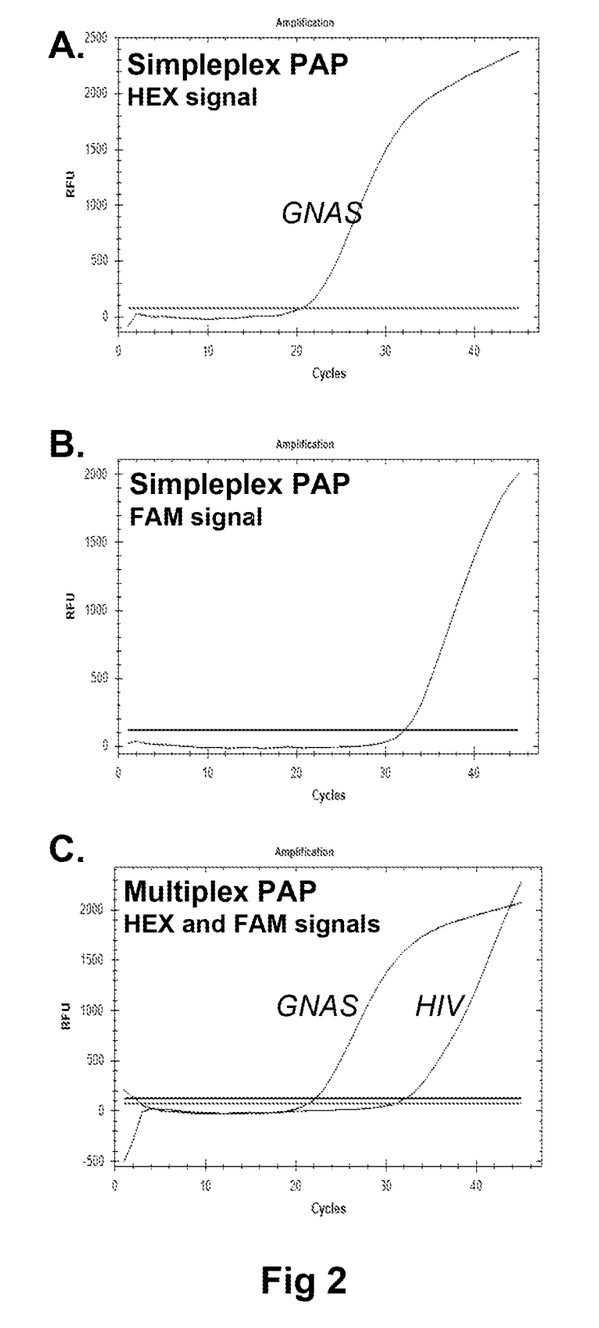

A multiplex PAP assay was tested that contains the GNAS and HIV assays in a reaction. The GNAS assay contains the forward fluorophore-quencher dual-labeled blocked primer (SEQ ID 1) and the reverse blocked primer (SEQ ID 2), and the HIV assay contains the forward fluorophore-quencher dual-labeled blocked primer (SEQ ID 3) and the reverse blocked primer (SEQ ID 5) (Table 2). To simulate the copy ratio of the GNAS to HIV templates in medical condition, 100,000 copies of the human wildtype genomic DNA (i.e., 330 ng) and 100 copies of the HIV plasmid DNA template were added to a reaction. When the GNAS and HIV genes were amplified, HEX and FAM fluorescence signals were generated and measured at Ct 21.4 and 32.0, respectively (FIG. 2C). Another forward fluorophore-quencher dual-labeled blocked primer (SEQ ID 4) was also tested with similar results. In addition, the non-template control did not generated HEX or FAM fluorescence signals above the thresholds, showing the specificities.

Thus, pyrophosphorolysis activated fluorescence was developed to measure PAP amplification in singleplex and multiplex PAP assays.

fluorophore-quencher dual-labeled blocked primer (SEQ ID 1) and another reverse-M2 primer which contains a C to A 3'-artificial mutation at the 3rd nucleotide from the 3' end (SEQ ID 7) (Table 3). When the GNAS gene was amplified from 100,000 copies of the human wildtype genomic DNA (i.e., 330 ng), HEX fluorescence signals were generated and measured at Ct 21.8 and 27.6 for the two GNAS assays. Compared with the GNAS regular-PAP assay (SEQ ID 1 and 2) in Example 2, Ct values of the two GNAS assays (SEQ ID 1 and 6, and SEQ ID 1 and 7) were delayed by up to 7.1 cycles.

A multiplex PAP assay was tested that contains the GNAS delayed-PAP assay (SEQ ID 1 and 6) and the HIV PAP assay (SEQ ID 3 and 5) in a reaction. Another multiplex PAP assay was also tested that contains the GNAS delayed-PAP assays (SEQ ID 1 and 6) and the HIV PAP assay (SEQ ID 1 and 7).

TABLE 2

Primers of the GNAS and HIV genes

| Gene | Primer pair | Sequence (5' to 3') (SEQ ID NO)[a,b] | 5' end or internal fluorophore[b] | 3' end quencher[b] | 3' end blocker[a] | Fluorophore-quencher dual-labeled |
|---|---|---|---|---|---|---|
| GNAS gene | Forward | 5'HEX-ACTCTGAGCCCTCTTT CCAAACTACT-TAMRA-ddC3' (SEQ ID 1) | 5' end HEX | TAMRA | ddCMP | Yes |
| | Reverse | 5'GTCTCAAAGATTCCA GAAGTCAGGACAddC3' (SEQ ID 2) | | | ddCMP | No |
| HIV gene | Forward | 5' TTGGAGGACA(FAM-T)CAAGCAGCCATGCA AA-TAMRA-ddU3' (SEQ ID 3) | Internal FAM | TAMRA | ddUMP | Yes |
| | Forward | 5'FAM-TTGGAGGACATCAAG CAGCCATGCAAA-TAMRA-ddU3' (SEQ ID 4) | 5' end FAM | TAMRA | ddUMP | Yes |
| | Reverse | 5' TGCTATGTCAGTTCC CCTTGGTTCTCddT3' (SEQ ID 5) | | | ddTMP | No |

Footnotes of Table 2.
[a]Each primer contains a 3' non-extendable, blocked nucleotide, such as ddCMP at the 3' end, and matches its starting template along the length.
[b]Fluorophore-quencher dual-labeled blocked primers (SEQ ID 1, 3 and 4) contain a fluorophore covalently attached to a nucleotide in the internal nucleotide or at the 5' end, and a quencher covalently attached to a dideoxynucleotide at the 3' end. The types of the fluorophore and quencher are also indicated.

Example 3 of Singleplex and Multiplex Delayed-Pap Assays of the Gnas and Hiv Genes Delayed-PAP was developed by introducing an artificial mutation into the 3' region of a blocked primer, which can delay the product accumulation to a later time or cycle in PAP amplification (U.S. patent application 62/683,725). Pyrophosphorolysis activated fluorescence was further demonstrated in such delayed-PAP assays.

A singleplex GNAS delayed-PAP assay was tested with a forward fluorophore-quencher dual-labeled blocked primer (SEQ ID 1) (Table 2) and a reverse-M1 primer which contains a G to T 3'-artificial mutation at the $5^{th}$ nucleotide from the 3' end (SEQ ID 6) (Table 3). Another singleplex GNAS delayed-PAP assay was also tested with the forward 100,000 copies of the human wildtype genomic DNA (i.e., 330 ng) and 100 copies of the HIV template were amplified in a reaction. For the GNAS gene, HEX fluorescence signals were generated and measured at Ct 22.0 and 27.9 for the two GNAS delayed-PAP assays, respectively. Compared with the GNAS regular-assay (SEQ ID 1 and 2) in Example 2, Ct values of the two GNAS delayed-PAP assays (SEQ ID 1 and 6, and SEQ ID 1 and 7) were delayed by up to 7.4 cycles. On the other hand, for the HIV gene, FAM fluorescence signals were generated and measured at Ct 33.4 and 32.7 for the two reactions of the HIV assay (SEQ ID 3 and 5), respectively, substantially consistent with Example 2.

Thus, pyrophosphorolysis activated fluorescence to measure PAP amplification of nucleic acid was demonstrated in singleplex and multiplex delayed-PAP assays.

TABLE 3

Primers of the GNAS gene containing 3'-artificial mutations

| Primer[a] | Sequence (5' to 3') (SEQ ID NO) | 3'-artificial mutation[c] | |
|---|---|---|---|
| | | Type | From the 3' end |
| Reverse-M1 | 5' GTCTCAAAGATTCCAGAAGTCAG TACAddC3' (SEQ ID 6)[b] | G to T | 5nt |
| Reverse-M2 | 5' GTCTCAAAGATTCCAGAAGTCAG GAAAddC3' (SEQ ID 7) | C to A | 3nt |

Footnotes of Table 3.
[a]For the GNAS gene, the two blocked primers for delayed PAP had 3'-artificial-mutations introduced to mismatch to their starting templates. Each of reverse-M1 and M2 primers (SEQ ID 6 and 7) was paired with a fluorophore-quencher dual-labeled blocked primer (SEQ ID 1).
[b]For this reverse-M1 primer, an artificial mutation T is indicated as bold and underlined case. In addition, ddC means dideoxynucleotide C at the 3'end.
[c]For the 3'-artificial-mutation, the type and location from the 3' end are also indicated in the 3' region. The nucleotide at the 3' end is assigned as 1.

REFERENCE

Deutscher M P, Kornberg A. 1969. Enzymatic synthesis of deoxyribonucleic acid. 28. The pyrophosphate exchange and pyrophosphorolysis reactions of deoxyribonucleic acid polymerase. J Biol Chem 244(11):3019-28.

Holland P M, Abramson R D, Watson R, Gelfand D H. 1991. Detection of specific polymerase chain reaction product by utilizing the 5'-3' exonuclease activity of *Thermus aquaticus* DNA polymerase. Proc. Natl. Acad. Sci. USA 88(16):7276-7280.

Liu Q, Nguyen V Q, Li X, Sommer S S. 2006. Multiplex dosage pyrophosphorolysis-activated polymerization: application to the detection of heterozygous deletions. Biotechniques 40(5):661-8.

Liu Q, Sommer S S. 2000. Pyrophosphorolysis-activated polymerization (PAP): application to allele-specific amplification. Biotechniques 29(5):1072-1080.

Liu Q, Sommer S S. 2002. Pyrophosphorolysis-activatable oligonucleotides may facilitate detection of rare alleles, mutation scanning and analysis of chromatin structures. Nucleic Acids Res 30(2):598-604.

Liu Q, Sommer S S. 2004a. Detection of extremely rare alleles by bidirectional pyrophosphorolysis-activated polymerization allele-specific amplification (Bi-PAP-A): measurement of mutation load in mammalian tissues. Biotechniques 36(1):156-66.

Liu Q, Sommer S S. 2004b. PAP: detection of ultra rare mutations depends on P* oligonucleotides: "sleeping beauties" awakened by the kiss of pyrophosphorolysis. Hum Mutat 23(5):426-36.

Liu Q, Sommer S S. 2004c. Pyrophosphorolysis by Type II DNA polymerases: implications for pyrophosphorolysis-activated polymerization. Anal Biochem 324(1):22-8.

Modrich P. 1987. DNA mismatch correction. Annu Rev Biochem 56:435-66.

The invention claimed is:

1. A plurality of pairs of forward and reverse 3' blocked primers comprise deoxyribonucleotides for multiplex pyrophosphorolysis activated polymerization (PAP) to amplify a plurality of template nucleic acids in a reaction, comprising:

a) a first pair of forward and reverse 3' blocked primers complementary to a first template nucleic acid, wherein the first forward or reverse primer comprises a first fluorophore covalently attached to a nucleotide in the internal region or at the 5' end and a universal quencher is covalently attached to a first non-extendable, blocked nucleotide which lacks the 3' hydroxyl group and is located at the 3' end of the primer, and wherein once the primer anneals to its template nucleic acid, the first non-extendable, blocked nucleotide attached with the universal quencher is removed from the 3' end of the primer by pyrophosphorolysis catalyzed by a polymerase to generate two products of 1) a 3' unblocked primer which is covalently labeled with the first fluorophore in the internal region or at the 5' end, and 2) a corresponding blocked nucleoside triphosphate which is covalently labeled with the universal quencher, thus the first fluorophore emits a fluorescence signal in PAP amplification, and b) a second pair of forward and reverse 3' blocked primers complementary to a second template nucleic acid, wherein the second forward or reverse primer comprises a second fluorophore covalently attached to a nucleotide in the internal region or at the 5' end and a universal quencher is attached to a second non-extendable, blocked nucleotide which lacks the 3' hydroxyl group and is located at the 3' end of the primer, and wherein once the primer anneals to its template nucleic acid, the second non-extendable, blocked nucleotide covalently attached with the universal quencher is removed from the 3' end of the primer by pyrophosphorolysis catalyzed by the polymerase to generate two products of 1) a 3' unblocked primer which is covalently labeled with the second fluorophore in the internal region or at the 5' end, and 2) a corresponding blocked nucleoside triphosphate which is covalently labeled with the universal quencher, thus the second fluorophore emits another fluorescence signal in PAP amplification.

2. The plurality of pairs of forward and reverse 3' blocked primers for multiplex pyrophosphorolysis activated polymerization of claim 1, wherein the first forward or reverse blocked primer has a FAM (carboxyfluorescein) fluorophore attached to a nucleotide in the internal region or at the 5' end and a universal TAMRA (carboxytetramethylrhodamine) quencher attached to the first non-extendable, blocked nucleotide at the 3' end, wherein the first non-extendable, blocked nucleotide is a dideoxynucleotide, and wherein the second forward or reverse blocked primer has a HEX (hexachlorofluorescein) fluorophore attached to a nucleotide in the internal region or at the 5' end and the same universal TAMRA (carboxytetramethylrhodamine) quencher attached to the second non-extendable, blocked nucleotide at the 3' end, wherein the second non-extendable, blocked nucleotide is a dideoxynucleotide.

3. The plurality of pairs of forward and reverse 3' blocked primers for multiplex pyrophosphorolysis activated polymerization of claim 1, wherein the first forward or reverse 3' blocked primer has the same universal quencher as the second forward or reverse 3' blocked primer, but has a different fluorophore than that of the second forward or reverse 3' blocked primer.

4. The plurality of pairs of forward and reverse 3' blocked primers for multiplex pyrophosphorolysis activated polymerization of claim 1, wherein the first template nucleic acid is an internal control nucleic acid and the second template nucleic acid is a target nucleic acid.

5. The plurality of pairs of forward and reverse 3' blocked primers for multiplex pyrophosphorolysis activated polymerization of claim 1, wherein emission spectrums of the fluorophores overlap an absorbance spectrum of the universal quencher.

6. The plurality of pairs of forward and reverse 3' blocked primers for multiplex pyrophosphorolysis activated polymerization of claim 1, wherein the fluorophores are located 30 bases or less from the 3' ends.

7. The plurality of pairs of forward and reverse 3' blocked primers for multiplex pyrophosphorolysis activated polymerization of claim 1, a) wherein the first forward or reverse 3' blocked primer comprises the universal quencher attached to the first non-extendable, blocked nucleotide at the 3' end, and wherein the first non-extendable, blocked nucleotide is a dideoxynucleotide, and b) wherein the second forward or reverse 3' blocked primer comprises the universal quencher attached to the second non-extendable, blocked nucleotide at the 3' end, and wherein the second non-extendable, blocked nucleotide is a dideoxynucleotide.

8. The plurality of pairs of forward and reverse 3' blocked primers for multiplex pyrophosphorolysis activated polymerization of claim 1, a) wherein the first forward or reverse 3' blocked primer comprises the universal quencher attached to the first non-extendable, blocked nucleotide at the 3' end, and wherein the first non-extendable, blocked nucleotide is an acyclonucleotide, and b) wherein the second forward or reverse blocked 3' blocked primer comprises the universal quencher attached to the second non-extendable, blocked nucleotide at the 3' end, and wherein the second non-extendable, blocked nucleotide is an acyclonucleotide.

* * * * *